(12) United States Patent
Takagi et al.

(10) Patent No.: US 10,874,826 B2
(45) Date of Patent: Dec. 29, 2020

(54) BALLOON CATHETER SYSTEMS

(71) Applicant: Terumo Corporation, Tokyo (JP)

(72) Inventors: Ayu Takagi, Tustin, CA (US); Hironori Takai, Newport Beach, CA (US)

(73) Assignee: Terumo Corporation, Tokyo (JP)

( * ) Notice: Subject to any disclaimer, the term of this patent is extended or adjusted under 35 U.S.C. 154(b) by 131 days.

(21) Appl. No.: 15/726,264

(22) Filed: Oct. 5, 2017

(65) Prior Publication Data

US 2018/0093071 A1  Apr. 5, 2018

Related U.S. Application Data

(60) Provisional application No. 62/404,647, filed on Oct. 5, 2016, provisional application No. 62/414,520, filed on Oct. 28, 2016.

(51) Int. Cl.
*A61M 25/00* (2006.01)
*A61M 25/10* (2013.01)

(52) U.S. Cl.
CPC ...... *A61M 25/0021* (2013.01); *A61M 25/104* (2013.01); *A61F 2250/0067* (2013.01); *A61M 2025/0098* (2013.01); *A61M 2025/1004* (2013.01); *A61M 2025/105* (2013.01); *A61M 2025/1081* (2013.01)

(58) Field of Classification Search
CPC .............. A61M 25/10; A61M 25/0668; A61M 2025/1079; A61M 2025/105; A61M 2025/1081; A61M 2025/1004; A61M 39/06; A61M 2039/062; A61M 2039/064; A61M 2039/0686; A61M 2039/0606; A61M 5/3157; A61M 25/0662; A61M 25/0097; A61M 2025/0675; A61M 2025/0188; A61M 25/104
See application file for complete search history.

(56) References Cited

U.S. PATENT DOCUMENTS

| | | | |
|---|---|---|---|
| 5,242,399 A | | 9/1993 | Lau et al. |
| 5,800,517 A | * | 9/1998 | Anderson ............... A61F 2/958 604/171 |
| 5,843,027 A | | 12/1998 | Stone et al. |
| 5,876,374 A | | 3/1999 | Alba et al. |
| 5,893,868 A | | 4/1999 | Hanson et al. |
| 6,093,173 A | | 7/2000 | Balceta et al. |
| 6,110,146 A | * | 8/2000 | Berthiaume .... A61M 25/09041 604/103 |

(Continued)

OTHER PUBLICATIONS

WIPO, U.S. International Search Authority, International Search Report and Written Opinion dated Feb. 1, 2018 in International Patent Application No. PCT/US2017/055422, 12 pages.

*Primary Examiner* — Tiffany Legette
(74) *Attorney, Agent, or Firm* — Inskeep IP Group, Inc.

(57) ABSTRACT

A balloon catheter and balloon system particularly useful with drug-coated balloons is described. In some embodiments, the balloon catheter system includes various features designed to address problems with drug rubbing off due to contract friction during delivery of the balloon—including by utilizing a protective sleeve to shield the drug-coated balloon. In some embodiments, the balloon catheter system includes an inner high-pressure balloon and an outer drug-coated balloon to mitigate the time associated with performing vessel dilation.

16 Claims, 10 Drawing Sheets

(56) References Cited

U.S. PATENT DOCUMENTS

| | | | |
|---|---|---|---|
| 6,152,944 A * | 11/2000 | Holman | A61F 2/0095 604/96.01 |
| 9,445,929 B2 | 9/2016 | Longo et al. | |
| 10,449,335 B2 | 10/2019 | Poker et al. | |
| 2002/0116045 A1 * | 8/2002 | Eidenschink | A61F 2/958 623/1.11 |
| 2004/0093005 A1 * | 5/2004 | Durcan | A61M 25/00 606/194 |
| 2007/0219612 A1 | 9/2007 | Andreas et al. | |
| 2009/0227949 A1 | 9/2009 | Knapp et al. | |
| 2010/0249490 A1 * | 9/2010 | Farnan | A61M 25/005 600/16 |
| 2010/0268123 A1 * | 10/2010 | Callahan | A61M 25/0668 600/588 |
| 2011/0137400 A1 | 6/2011 | Dorn et al. | |
| 2012/0296313 A1 * | 11/2012 | Andreacchi | A61M 25/0668 604/509 |
| 2014/0221831 A1 * | 8/2014 | Kurrus | A61M 5/007 600/434 |
| 2015/0352340 A1 | 12/2015 | Ewing et al. | |
| 2016/0074632 A1 | 3/2016 | Moehl et al. | |

\* cited by examiner

BALLOON CATHETER SYSTEMS

RELATED APPLICATIONS

This application claims priority to U.S. Provisional Application Ser. No. 62/404,647 filed Oct. 5, 2016 entitled Balloon Catheter Systems, and to U.S. Provisional Application Ser. No. 62/414,520 filed Oct. 28, 2016 entitled Balloon Catheter Systems, both of which are hereby incorporated herein by reference in their entireties.

BACKGROUND OF THE INVENTION

Stenosis or restenosis is a narrowing of a blood vessel due to the buildup of sclerotic material. Stenosis can cause a variety of vascular conditions associated with reduced blood flow including stroke, heart disease, or limb loss. Drug coated balloons utilizing a variety of anti-sclerotic drugs such as Paclitaxel, Sirolimus, and/or Zotarolimus are one way of treating stenosis—the balloons are inflated to compact the sclerosis and the drugs are delivered to the vessel wall to help treat the region. Often, significant amounts of the drugs can be lost from the balloon during loading and tracking through the guiding sheath. Further, even when sufficient drug coatings are delivered to a target site, the delivery may be further hindered by the failure of the cylindrical balloon to conform to an abnormal vessel profile (e.g., non-circular) or where calcification on the vessel is particularly dense.

In this regard, there is a need for a balloon catheter system that can improve drug loss from a balloon and thereby improve drug during delivery to the vessels of a patient. There is also a need for a balloon catheter that can provide improved treatment to a sclerotic region in which a typical balloon may not conform to the shape of the target region, a calcified sclerosis, or a relatively dense sclerosis.

SUMMARY OF THE INVENTION

In some embodiments, a protective sleeve for a drug coated balloon is described. The protective sleeve is useful to prevent a drug coating from rubbing off of a balloon when inserted and tracked through a guiding sheath to a target treatment site.

In one embodiment, the protective sleeve is configured so that the drug coated balloon can be placed within a tubular section of the protective sleeve and the protective sleeve and enclosed drug coated balloon are pushed through the guiding sheath. In one embodiment, the protective sleeve includes a distal nose-cone to help prevent blood from rubbing off a drug coating from the balloon. In one embodiment, the tubular section of the protective sleeve housing the drug coated balloon can be narrowed to limit the balloon's exposure to blood.

In one embodiment, the protective sleeve has a relatively small length, being sized to cover only the drug-coated balloon itself as it is inserted into a hemostasis valve of the guiding sheath. In one embodiment, the protective sleeve is part of the balloon catheter assembly and can be removed from the balloon catheter and then placed into the hemostasis valve to aid with placing the drug coated balloon into the guiding sheath.

In some embodiments, a balloon catheter and balloon catheter system utilizing a protective sleeve is described. The protective sleeve is useful to prevent a drug coating from rubbing off of a balloon when tracked through a guiding sheath to a target treatment site.

In one embodiment, a balloon catheter system, including a balloon catheter, utilizes a protective sleeve in which the balloon catheter is placed prior to loading the balloon catheter through a guiding sheath. The balloon protective sleeve and the enclosed balloon are tracked through the guiding sheath. In one embodiment, the balloon catheter/balloon catheter system utilizes a distal nose cone which helps protect the balloon from blood during delivery of the balloon, where premature exposure to blood during delivery could otherwise push drug off the balloon. In one embodiment, the tubular section of the protective sleeve housing the drug coated balloon can be narrowed to limit the balloon's exposure to blood.

In one embodiment, a balloon catheter/balloon catheter system utilizes a relatively short-length protective sleeve which is sized to aid in placing the drug coated balloon within the hemostasis valve of the guiding sheath. In some embodiments, the protective sleeve can come pre-attached to the balloon catheter, in which the protective sleeve is removed from the balloon catheter and placed into the hemostasis valve to aid with placing the drug coated balloon into the guiding sheath.

In some embodiments, a balloon catheter is described. The balloon catheter has particular utility in treating stenotic regions of the vasculature which may have an irregularly shaped buildup of sclerosis, or stenotic regions with particularly thick or dense sclerosis.

In one embodiment, the balloon catheter utilizes a double balloon including an inner balloon and an outer balloon. The inner balloon is a high-pressure balloon and the outer balloon is drug-coated and highly compliant in order to conform to the stenotic vessel shape.

In one embodiment, a method of using a balloon catheter which includes a high-pressure inner balloon and a drug-coated, compliant outer balloon is described. The outer balloon is first inflated in order to conform to the stenotic vessel shape, the outer balloon delivers drugs to the sclerosis-containing vessel. The outer balloon is then deflated. The high-pressure inner balloon is then inflated in order to compress the sclerosis so that a relatively consistent lumen is formed within the vessel.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
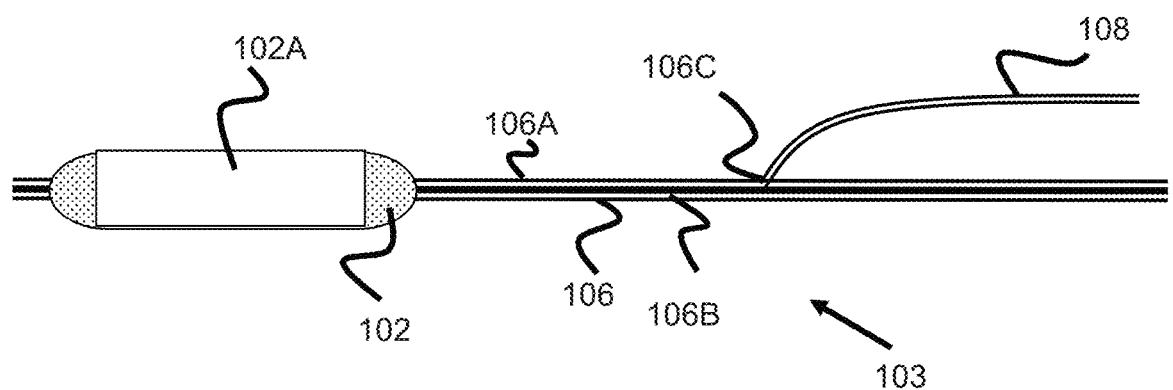
FIG. 1a illustrates a typical drug-coated balloon which is part of a balloon catheter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Drug-coated balloons are used for a variety of vascular conditions, including stenosis—which is a condition where sclerotic material builds up in the blood vessels, affecting the normal circulation of blood through the vasculature. Restenosis is the continued occurrence of stenosis where treatment to treat the sclerosis is unsuccessful and results in the continued existence and buildup of sclerotic material within the vasculature.

One method of treating stenosis is the use of a drug coated balloon. These drug coated balloons can be used in several target areas, including for treatment of stenosis in the superficial femoral or popliteal arteries which are larger arteries in the legs. Typically, this procedure involves a balloon catheter having a drug coated balloon on its distal end. Various anti-sclerotic drugs can be coated onto the balloon, such as Paclitaxel, Sirolimus, and/or Zotarolimus. The balloon is tracked through a larger guiding sheath to the target treatment site. The balloon is then delivered and inflated at the stenosis site to compress the sclerotic material and deliver drug to the vessel wall to prevent the future buildup of sclerotic material.

One complication with delivery of drug coated balloons is that the drug coating can rub off the balloon. This can occur primarily in two scenarios—first, when the drug coated balloon is initially placed through the hemostasis valve of the guiding sheath for entry into the guiding sheath (where most of the drug loss typically takes place). Second, when the drug coated balloon is being pushed through the guiding sheath. This drug loss is due to contact friction between the balloon and, respectively, the hemostasis valve and the inner surface of the guiding sheath. Drug loss during placement and tracking can limit the amount of drug that is available to treat the stenosis and can enhance the chance of continued stenosis or restenosis since less drug is available to treat the problem region.

This is particularly problematic in larger arteries, such as the superficial femoral and popliteal arteries, since the stenotic regions can become particularly large and calcified due to the relatively larger vessel size and therefore may need a large drug dose to treat the target region. Drug loss is therefore a significant problem associated with the use of drug coated balloons.

Embodiments herein include protective sleeves designed to help protect the drug coated balloon during placement within the hemostasis valve of the guiding sheath as well as during tracking through the larger guiding sheath. For the purposes of the figures discussed in the description, unless noted otherwise anything on the left is considered "distal" or in the direction of the patient body/vasculature, while anything on the right is considered proximal or in the direction outside of the patient body/vasculature.

FIG. 1*a* shows a typical drug-coated balloon catheter 103 having an inflatable drug-coated balloon 102 mounted on the distal end of the catheter 103 and in which a portion of the balloon has a drug coating 102A. Preferably, substantially all of the length and circumference of the balloon 102 includes the drug coating 102A. Often, the proximal and distal tapered ends of the balloon 102 are free of the drug coating, since these portions are unlikely to contact the vessel.

The drug-coated balloon catheter 103 includes an elongated body portion 106 having a first lumen 106A located along all or a portion of the length of the body portion 106 and through which a guidewire 108 can be advanced (and/or a contrast agent or therapeutic material can be delivered within the patient). A second inflation lumen 106B extends from a proximal end of the body portion 106 to an opening within the balloon 102, allowing for delivery of inflation media during a procedure.

Balloon catheters also often include a separate rapid exchange port 106C at some distal location along the body portion 106 and lumen 106A to allow quicker placement and removal of the guidewire 108, as shown in FIG. 1*a*. Balloon catheters 103 are typically placed into a hemostasis valve of a guiding sheath and then are delivered through the guiding sheath for delivery to a target treatment area, however, as discussed above, there is significant drug loss associated with these steps.

Figure 1B:
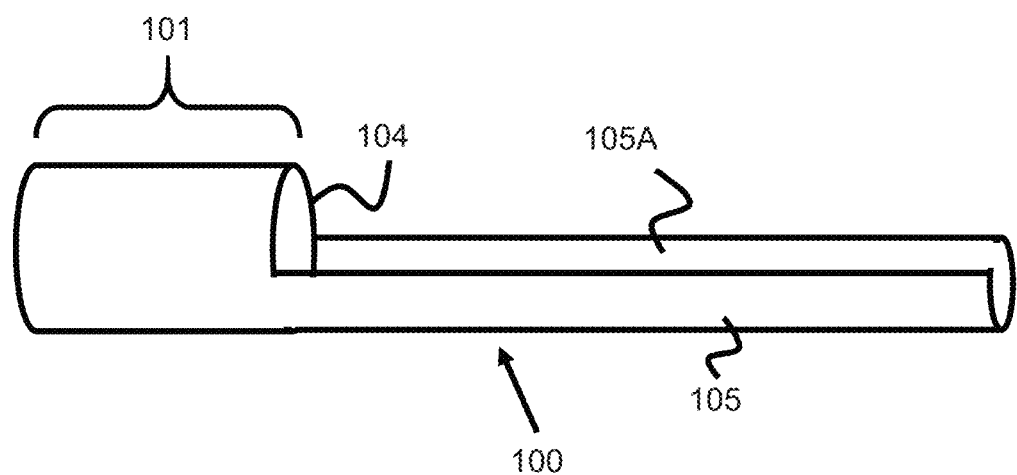
FIG. 1b illustrates a balloon protective sleeve according to one embodiment.

FIG. 1*b* illustrates a protective sleeve 100 according to one embodiment to protect the drug-coated balloon 102 of the drug-coated balloon catheter 103 during placement through the hemostasis valve of the guiding sheath and passage through the guiding sheath. The protective sleeve 100 includes a distal tubular section 101 and a proximal body portion 105 having an arc-shaped channel or "half-pipe" shaped region 105A that extends to the proximal end of the body portion 105 that forms an opening 104 to the distal tubular section 101.

Figure 1C:
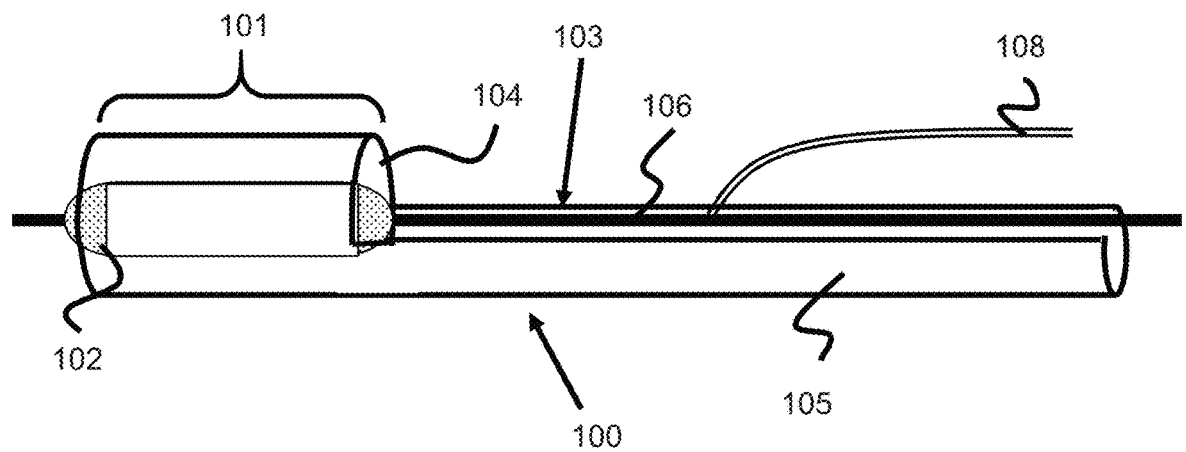
FIG. 1c illustrates the drug-coated balloon of FIG. 1a within the protective sleeve of FIG. 1b.
Figure 2:
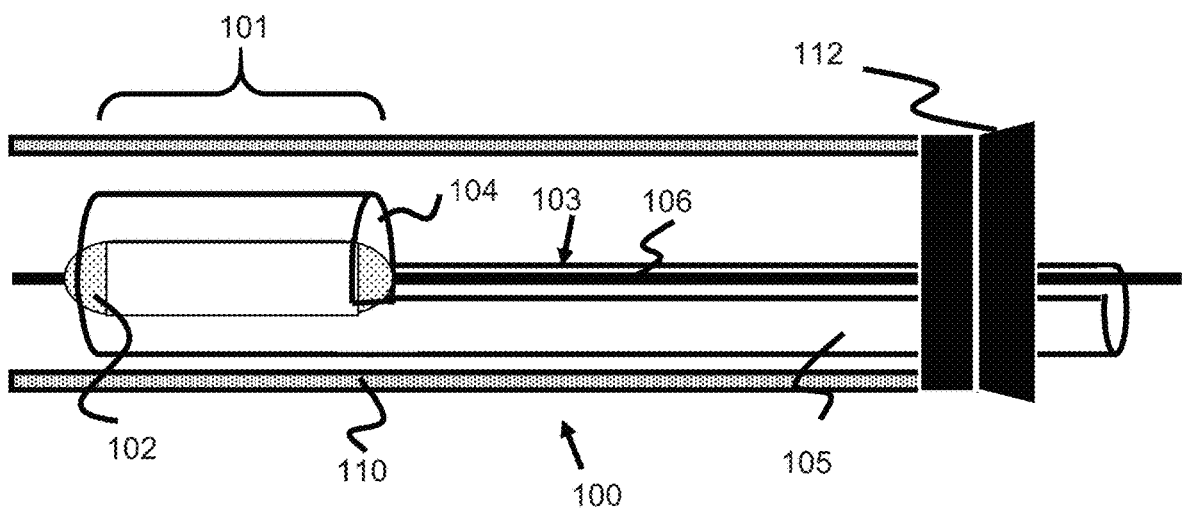
FIG. 2 illustrates the balloon protective sleeve of FIG. 1 within a larger guiding sheath.

As best seen in FIG. 1*c*, the balloon 102 is advanced within the distal tubular section 101, since both the proximal aperture 104 and internal diameter of the section 101 are larger than the deflated diameter of the balloon 102. The body portion 106 of the catheter 103 can be positioned within the non-tubular arc-shaped region 105A. Preferably, the protective sleeve 100 is placed over the catheter 103, with the balloon already inside of the distal tubular section 101 prior to placement within the hemostasis valve 112 of guiding sheath 110 and is then pushed through guiding sheath 110—as shown in FIG. 2.

Protective sleeve 100 provides an intermediate surface to protect the balloon from direct contact with the hemostasis valve 112 when the drug-coated balloon 102 enters the guiding sheath 110, as well as an intermediate surface to protect the drug-coated balloon 102 from direct contact with the inner diameter of the guiding sheath when tracked through said guiding sheath 110. Drug loss primarily occurs during placement through the hemostasis valve 112 (due to the reduced diameter of the hemostasis valve, as well as the rough texture of the hemostasis valve) and secondarily during tracking through the guiding sheath 110. The protective sleeve 100 reduces or eliminates these problems by protecting the drug-coated balloon 102 when it enters the hemostasis valve 112 and during tracking through the guiding sheath 110. The protective sleeve 100 should be sized to fit within the inner diameter of the guiding sheath 110 so it can be advanced through the guiding sheath 110. The external surface of the balloon protective sleeve 100 can utilize a hydrophilic or other friction-reducing coating to reduce friction with the external guiding sheath 110. The balloon protective sleeve 100 may also be made of a lubricious polymer to reduce friction between the overlying guiding sheath 110 and underlying protective sleeve 100.

The protective sleeve 100 is advanced by the physician at its proximal end to so as to also advance the enclosed balloon catheter 103 through guiding sheath 110. As previously discussed, the proximal section 105 of the protective sleeve 100 is not a fully enclosed tube like distal section 101, but rather an arc-shaped or "half-pipe" shaped region 105A. This configuration increases the ease of loading the drug coated balloon 102 since the balloon 102 must only be pushed through cut-out aperture 104 to access the distal tubular section 101 instead of being pushed through the entire length of the balloon protective sleeve 100, which would be the case if the entire length of the balloon protective sleeve 100 had a completely enclosed tubular shape. Since the body portion 106 resides in the arc-shaped portion 105A of the protective sleeve 100, the physician can advance both the sleeve 100 and the catheter 103 together by manipulating only the proximal end of the proximal body portion 105 (or optionally both proximal ends of the proximal body portion 105 and the catheter 103). In this way, the proximal body portion 105 can be thought of as a navigational section since a user grips the proximal part of proximal body portion 105 to move protective sleeve 100 along with the enclosed balloon catheter 103 and drug coated balloon 102.

After passing through guiding sheath 110 and being placed at the target treatment site, the drug coated balloon 102 is exposed in one of a few ways. First, the protective sleeve 100 is pushed out from the guiding sheath 110 or the guiding sheath 110 is proximally withdrawn to expose the distal tubular section 101 of protective sleeve 100. Then, the protective sleeve 100 is retracted to expose drug coated balloon 102, the balloon catheter is pushed out from the protective sleeve 100, or both techniques can be performed together (in a dual push/pull method). Since the drug-coated balloon 102 is located within the protective sleeve 100, a small amount of drug loss due to friction between the drug-coated balloon 102 and the protective sleeve 100 may be possible, however this drug loss is much less than the amount that would otherwise occur without the sleeve 100. To further mitigate drug loss from the balloon 102, the inner surface of protective sleeve 100 may include a hydrophilic or otherwise friction-reducing coating, or be made of a lubricious polymer.

Figure 3A:
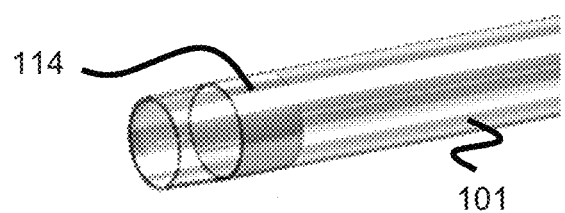
FIG. 3a illustrates the distal end of the balloon protective sleeve of FIG. 1.

The distal end of the distal tubular section 101 may further include a radiopaque (e.g. tantalum) marker band 114, as seen in FIG. 3a. Guiding sheaths 110 often include a marker band at about 3 cm from the distal tip so that a device delivered through the guiding sheath can be aligned with the distal tip to ensure proper placement relative to the guiding sheath 110. In this respect, the marker band 114, when aligned with the marker band of guiding sheath 110, helps the user ascertain that the protective sleeve is at the distal end of the guiding sheath.

Figure 3B:
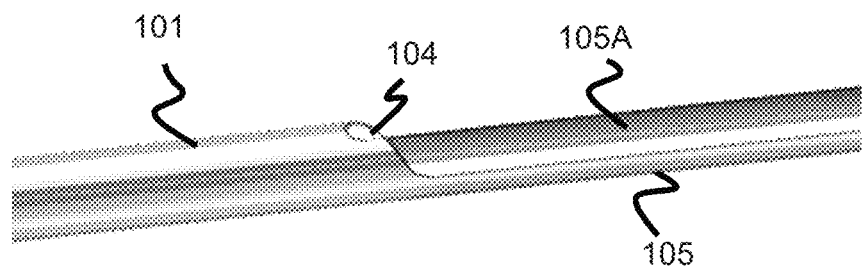
FIG. 3b illustrates a proximal cut-out section of the balloon protective sleeve of FIG. 1.

The aperture 104 created between the distal tubular region 101 and the channel 105A can be formed from a generally perpendicular wall cut (i.e., a cut perpendicular to the elongated axis of the sleeve 100, as seen in FIG. 1b, or can be cut at an angle that decreases in the proximal direction, as seen in FIG. 3b (e.g., 45 degrees or an angle less than 90 degrees) to create a transition between the two regions 101, 105A. In one example, the protective sleeve 100 can be manufactured by cutting a portion of a tube between the aperture 104 and the proximal end of the proximal section 105, thereby forming the arc-shaped or channel portion 105A. In another example, a distal tubular section 101 can be connected to an entire tube cut lengthwise to form the proximal portion 105.

Figure 4:
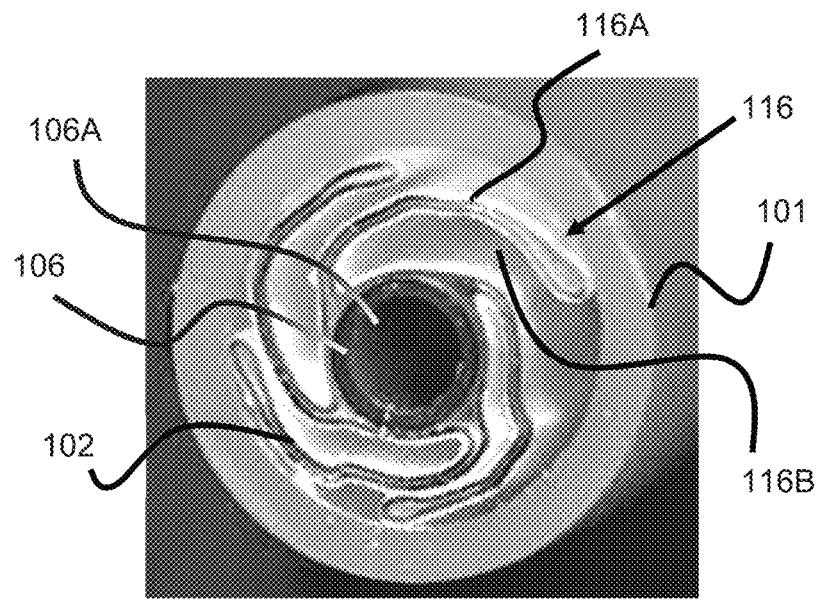
FIG. 4 illustrates a balloon within a balloon protective sleeve.

Drug coated balloons are often pleated, as shown in FIG. 4, to reduce the amount of drug that can potentially be lost. The pleat 116 includes an outer region 116A which may contact the surface overlying the balloon 102 and an inner region 116B which is protected from the overlying surface. This pleated design helps ensure the entire surface of the balloon is not exposed and thereby limits the amount of drug that is lost during placement and tracking.

The drug coated balloon 102, as discussed earlier, includes a lumen 106A that accommodates a guidewire 108, shown in FIG. 1A, and provides a path for any subsequently introduced therapeutic materials that may be used in the treatment area. The proximal end of balloon 102 is connected to an inflation lumen 106B to allow inflation media (e.g. liquid contrast agent) to be injected through a port in the catheter body 106 to inflate the balloon 102 once deployed in the target treatment site in the vasculature.

Figure 5:
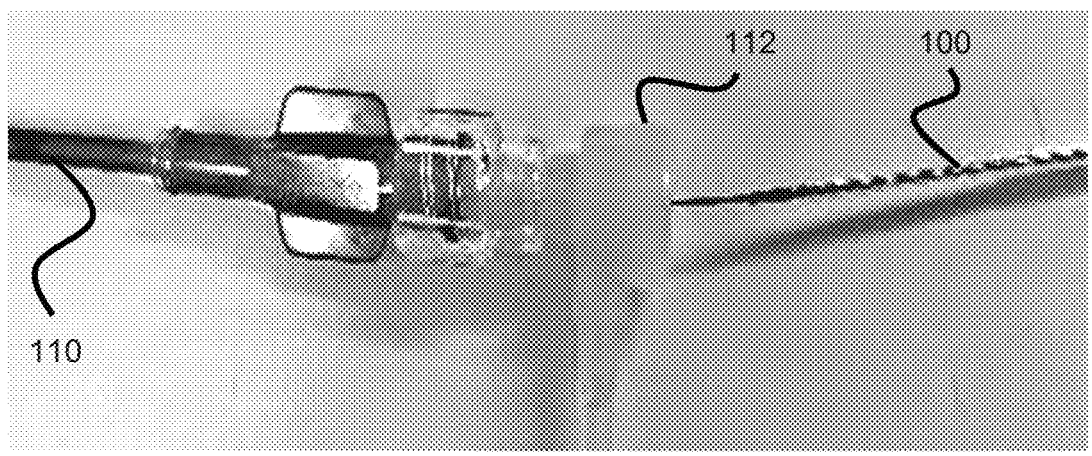
FIG. 5 illustrates the balloon protective sleeve of FIG. 1 being placed within a hemostasis valve of a guiding sheath.

FIG. 5 shows the balloon and balloon protective sleeve 100 being placed within the hemostasis valve 112 of guiding sheath 110, for tracking through said guiding sheath 110. Various embodiments are contemplated regarding the placing of balloon within protective sleeve 100. In one embodiment, the balloon 102 is preplaced within distal tubular section 101 of protective sleeve 100 and sold as a package to the end user. In another embodiment, the end user physically places the balloon 102 within distal tubular section 101 of protective sleeve 100, for example by pushing the balloon 102 through aperture 104 of protective sleeve 100. Once the balloon is within the protective sleeve 100, the protective sleeve 100 is physically placed within the hemostasis valve 112 and pushed through guiding sheath 110 in the manner described earlier. Please note, in the embodiment where the end user would place the balloon within the distal tubular section 101 of protective sleeve 100, the balloon 102 may need to be placed within a temporary protective structure to prevent drug loss during the storage and shipping process—this temporary protective structure would then be removed by the end user when said user places the balloon within the distal tubular section 101 of protective sleeve 100.

Other embodiments of the protective sleeve 100 can forego cut-out region 105A and instead is entirely tubular. With this embodiment, it would be beneficial for the protective sleeve 100 to be sold/delivered pre-loaded with the drug coated balloon 102 to the end-user to minimize the effort needed to track the balloon through a fully tubular protective structure.

Figure 6:
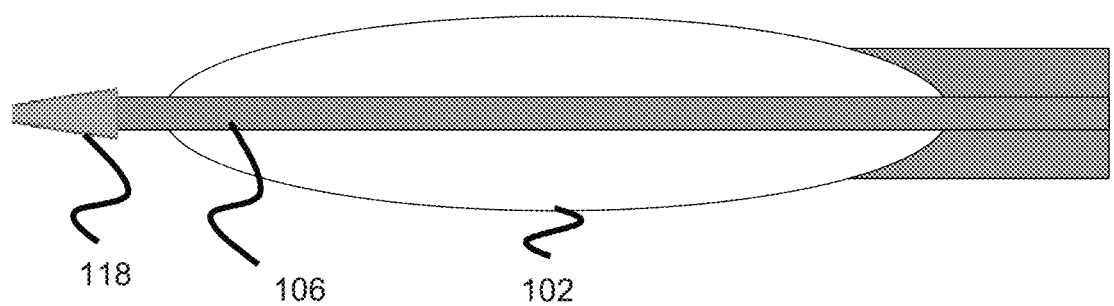
FIG. 6 illustrates a balloon protective sleeve utilizing a distal nose cone.
Figure 7:
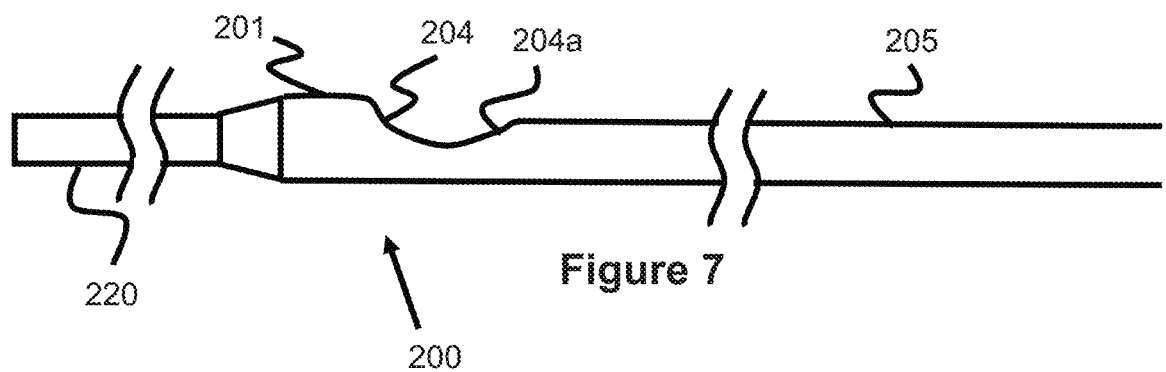
FIG. 7 illustrates a side view of a balloon protective sleeve with a narrow distal section.
Figure 8:
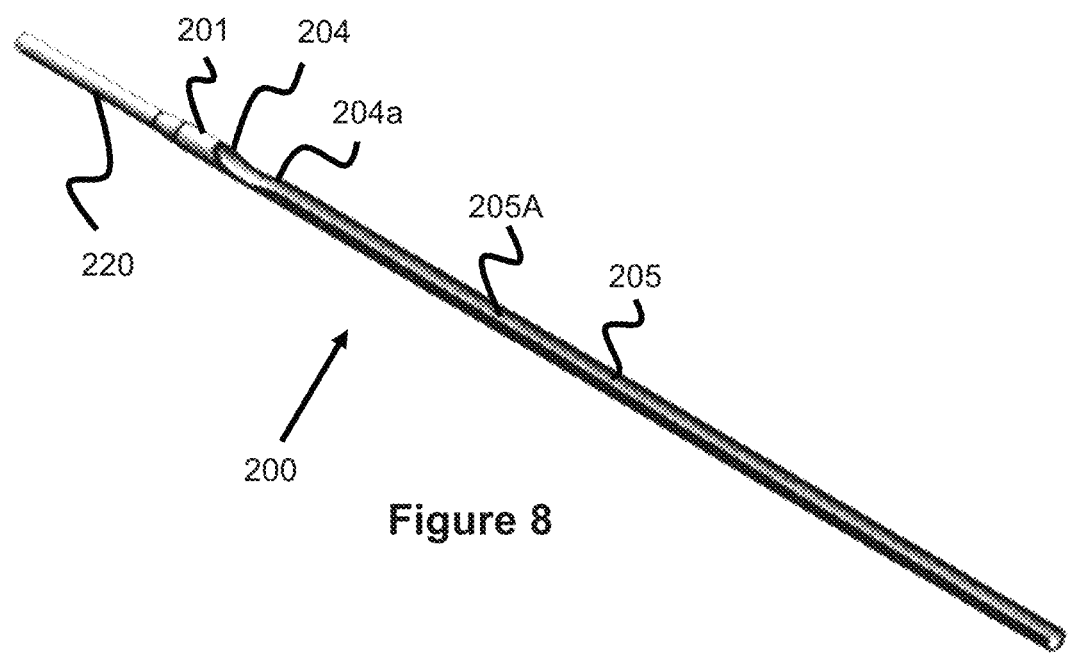
FIG. 8 illustrates another view of the balloon protective sleeve of FIG. 7.

The earlier discussion highlighted placement of a drug-coated balloon 102 within a guiding sheath 110, as well as tracking the balloon 102 through the guiding sheath 110, as the primary scenarios where drug loss can occur. However, exposure to blood can also cause drug loss from the drug coated balloon 102. Generally, once the drug-coated balloon 102 is tracked to the distal end of the guiding sheath 110, the distal part of the drug-coated balloon 102 may contact blood even before the balloon 102 is deployed, and the pressurized flow of blood may cause of the drug coating 102A to be removed from the balloon 102. The protective sleeve 100 can address some of these issues by limiting the amount of balloon surface which the blood can contact due to the surface area of the protective sleeve 100. However the protective sleeve 100 alone may not entirely prevent drug loss due to blood contact. FIGS. 6-8 describe various embodiments to reduce this drug loss due to blood contact/blood flow.

In FIG. 6, a nose cone 118 is attached to the distal end of catheter body 106, past the distal end of balloon 102 that helps block or redirect direct blood flow contact with the balloon 102, thereby further reducing loss of the drug coating 102A. The nose cone 118 is either disposed around the catheter body 106 or includes a passage through it that is aligned with the lumen 106A, such that the nose cone 118 provides an outlet for a guidewire or other agents advanced through the lumen 106A. Preferably, the nose cone 118 can be a proximally-increasing conical shape as pictured or similar ramped shape so that the proximal end of the cone has the greatest thickness to prevent blood from prematurely contacting the balloon during delivery, while the distal end has a smaller profile in order to not materially impede blood flow once the balloon is placed within the vasculature. However, a variety of shapes are contemplated including cones, cylinders, elliptical, ovular, and/or bullet-like shapes.

In one embodiment, the nose cone 118 is located within the balloon protective sleeve 110 and the proximal end of the nose cone 118 has a diameter similar to the inner diameter of the balloon protective sleeve 100, thereby preventing blood from contacting the drug-coated balloon 102. In another embodiment, the nose cone 118 is located distal to balloon protective sleeve 110 and the proximal end of nose cone 118 is has a diameter similar to the inner diameter of guiding sheath 110.

Blood-induced drug coating loss can also be addressed by narrowing the distal end of the balloon protective sleeve so that there is less available space for the blood to contact the drug-coated balloon 102. FIGS. 7-8 illustrate one such embodiment, in which a balloon protective sleeve 200 has a diametrically narrowed distal section 220 relative to the proximal portion of the distal tubular section 201. The narrowed distal section 220 accommodates all of the balloon 102 or solely the distal part of the balloon as the balloon 102 is being housed within the protective sleeve while tracking through the guiding sheath 110. Narrowed distal section 220 has a smaller diameter compared to the rest of the distal tubular section 201 (which accommodates the balloon 102) of protective sleeve 200 and therefore sits tighter relative to the balloon, limiting the space for blood to enter. This mitigates the chance that blood can enter and remove the drug coating 102A from the balloon 102.

Narrowed distal section 220 shown in FIGS. 7-8 can be used instead of the nose cone 118 shown in FIG. 6, or can be used along with nose-cone 118 to provide multiple levels of protection to help prevent blood from pushing or washing the drug coating 102A off of the balloon.

Various embodiments of the narrowed distal section 220 embodiment are contemplated. For instance, the entire section that the drug-coated balloon 102 is located within can be relatively narrow. Alternatively, just a distal part is narrowed such that a proximal section of the balloon 102 is located in an enlarged proximal section while the distal section of the balloon is located within a narrowed section 220.

An alternative embodiment utilizing the narrowed distal section 220 described above can utilize a fuller distal section that the balloon sits within (sized similar to tubular section 101 in FIGS. 1-2), then a smaller narrowed distal section 220 beyond this balloon, where the narrowed section would limit the amount of blood that could enter the protective sleeve and contact the drug coated balloon 102.

The earlier description discussed how the balloon catheter 103 (of which drug coated balloon 102 is a part), is tracked through guiding sheath 110 by pushing/pulling the proximal end of the protective sleeve 100, which in turn conveys the balloon catheter 100 (and drug coated balloon 102) since the balloon catheter is contained within protective sleeve 100. The proximal section 105 of the protective sleeve 100 is not tubular in several of the embodiments to ease placement of the drug coated balloon 102 within the protective sleeve 100. However, one drawback to this arrangement is that since the proximal part 105 of the protective sleeve 100 is cut-away to form a channel 105A, there is less axial strength or kink resistance to the protective sleeve 100 due to the smaller cross-sectional area.

In FIGS. 7-8, the proximal section 205 of the protective sleeve has a greater curvature to the arc of its channel 205A compared to the channel 105A shown in the embodiment of FIGS. 1-3*b*, which is accomplished by making a more scalloped cut at region 204 (i.e., a cut of increased circumference/width) to define the entry point for the drug coated balloon. This scalloped cut is defined by a divot or inward tapered cut region 204*a* which creates enough of a gap, entry, space, or port to accommodate the drug coated balloon 102 within the distally placed tubular section 201, which may not otherwise fit due to the relatively narrow channel 105A opening. This proximal section 105 with a smaller opening of the channel 205A may be used in any of the protective sleeve embodiments to augment the push strength of the protective sleeve.

The primary locations in which loss of the drug coating can occur when tracking a drug coated balloon through a guiding sheath, as discussed earlier, are during placement within a hemostasis valve 112 of a guiding sheath 110 as well as during tracking through the guiding sheath 110—where the hemostasis valve 112 is the location where the greatest amount of drug coating 102A is lost. Loss of drug coating 102A occurs due during placement through the hemostasis valve 112 for a few reasons. First, the smaller diameter of the hemostasis valve 112 compared to the guiding sheath diameter causes increased contact friction with the balloon 102 when the balloon 102 is placed through the hemostasis valve 112. Second, the hemostasis valve port is not smooth which can promote loss of drug coating 102A due to friction. Third, drug-coated balloons 102 are fairly soft, meaning the physician generally must grip the balloon 102 to propel it through the hemostasis valve 112, which causes loss of the drug coating due to touch. Finally, retrograde blood flow through the hemostasis valve 112 can also cause drug loss due to contact with blood. The following embodiments are directed to a relatively shorter protective sleeve that functions solely to protect the drug coated balloon 102 when its inserted into the hemostasis valve 112—which is the primary scenario where blood loss occurs, but does necessarily not protect the balloon 102 while it is tracked through the guiding sheath 110.

Figure 9:
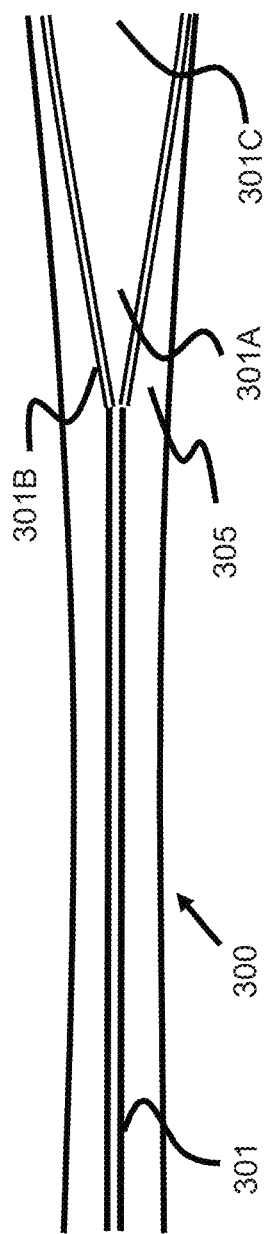
FIG. 9 illustrates a shortened balloon protective sleeve used solely to track the drug coated balloon through a hemostasis valve of a guiding sheath.

FIG. 9 illustrates a shortened protective sleeve 300 which can also be considered an insertion sleeve 300 since the function of the sleeve is to protect the drug-coated balloon 102 solely during insertion through the hemostasis valve 112 of a guiding sheath 110. Since protective sleeve 300 only protects the balloon during insertion into the hemostasis valve 112 it can be much shorter than protective sleeve embodiments 100 and 200 in FIGS. 1-8 which must span the complete length of the guiding sheath 110.

The protective sleeve 300 can be placed over the balloon 102 when the balloon 102 is placed inside the hemostasis valve 112 of guiding sheath 110 to protect the drug-coated balloon from drug loss when being placed within said hemostasis valve 112. The protective sleeve 300 has a thin cut 301 extending along its entire length (e.g. a cut 301a defining an opening that is 0.002 inches or less), forming a cross-sectional c-shape instead of a completely oval/circular shape. One end of protective sleeve 300 is preferably flared or radially opened to form a flared end 305 (i.e., the cut 301A increases in width in the proximal direction). In one example, the protective sleeve 300 is formed as a cylinder but the cut 301A in section 305 is larger than cut 301 in the rest of the sleeve causing flared end 305 to adopt its flared shape—meaning the larger shape of the flared end is due to the larger cut used in region 305. As shown in FIG. 9, cut 301A is tapered such that the cut size in end section 301C is larger than the cut size in section 301B. In one example, the cut-size in end section 301C defines an opening of about 0.17 inches to about 0.23 inches. The protective sleeve 300 is about 2.75-3.25 inches in length and the flared end is about 0.5 to 1 inch in length. In another example, protective sleeve 300 is about 3 inches, about 7.62 centimeters, or about 8 centimeters in length and flared end 305 is about 0.75 inches in length. Protective sleeve 300 can be formed from a variety of materials including a polymeric material such as Pebax 7233 SA01. In one example, protective sleeve 300 has an inner diameter of about 0.1 inches and an outer diameter of about 0.115 inches. Since protective sleeve 300 is generally formed from a cylinder which is given a larger cut in region 301C to adopt the flared end 305 as described earlier, the protective sleeve diameter can be thought of as the outer diameter of the sleeve plus the size of the cut. Using this approach, the protective sleeve's flared end 305 diameter is about 0.285 inches to 0.345 inches, or about 0.315 inches—while the protective sleeve's diameter in the non-flared portion of the sleeve is about 0.115 inches to 0.12 inches, or about 0.117 inches.

Figure 10:
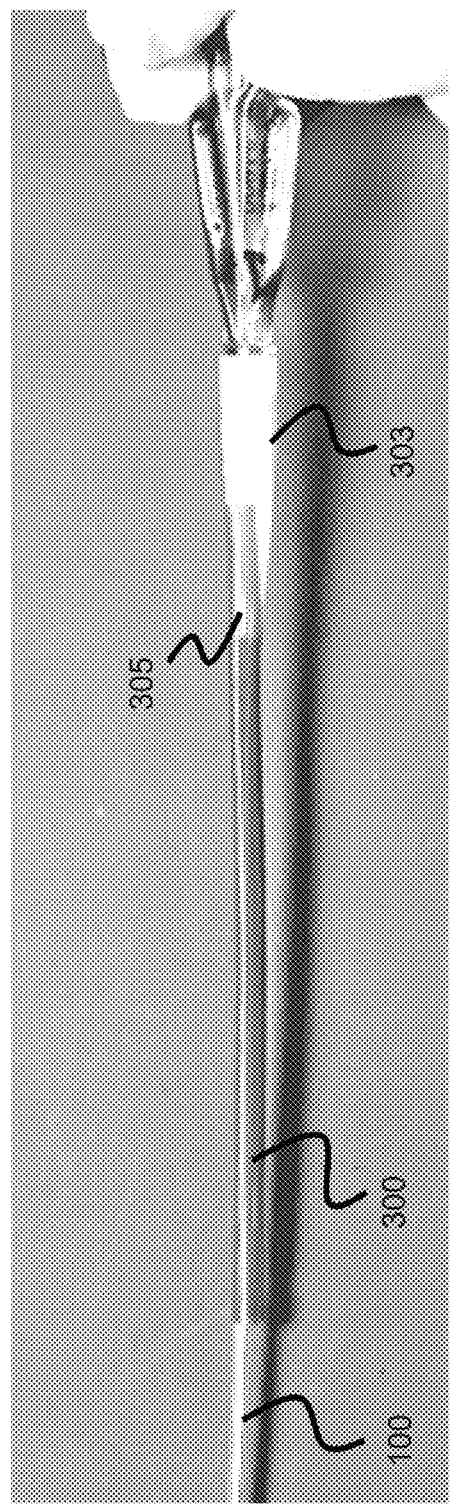
FIG. 10 illustrates the shortened balloon protective sleeve of FIG. 9 pre-mounted to a proximal region of a balloon catheter.

FIG. 10 shows an embodiment in which the protective sleeve 300 is preplaced on the proximal part of the balloon catheter 103, where the balloon catheter 100 is sold to the end user with the protective sleeve 300 already located on the proximal part of said balloon catheter 100. The proximal end of protective sleeve 300 (which coincides with flared end 305) would sit over the enlarged strain relief 303 of the balloon catheter 103.

Proximal flare 305 is useful for a couple purposes. First, the flare provides a slightly enlarged region to better fit over strain relief 303. Second, the proximal flare 305 provides a smoother entry for the drug coated balloon when said balloon is loaded through said protective sleeve 300. Comparing FIG. 9 and FIG. 10, cut 301 would sit on the bottom of protective sleeve 300 shown in FIG. 10. The user can simply remove protective sleeve 300 from the balloon catheter 103, and then place the protective sleeve 300 within the hemostasis valve of the guiding sheath in a manner that will be explained in more detail below.

Figure 11:
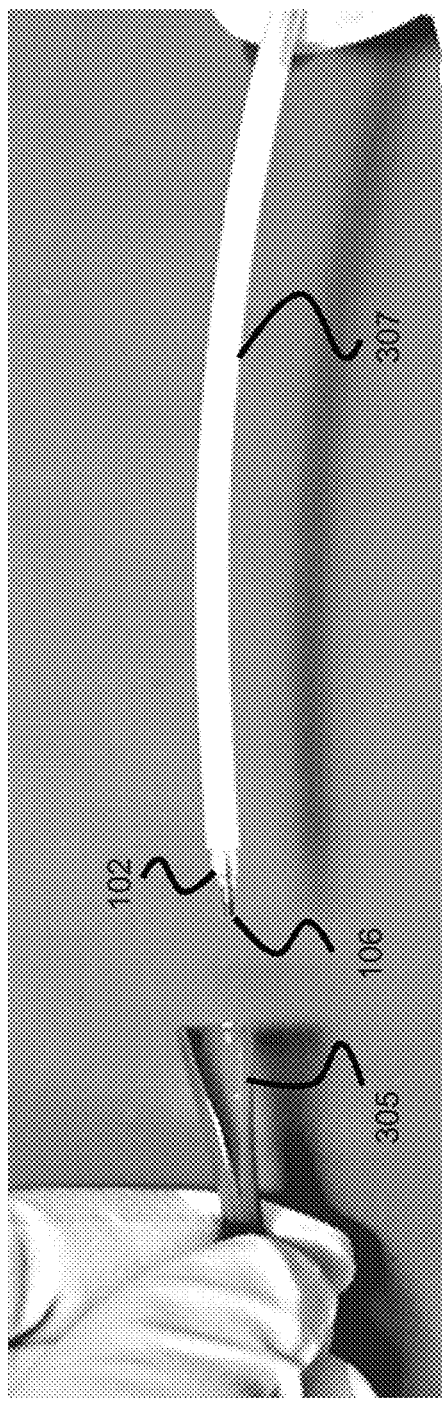
FIG. 11 illustrates a drug coated balloon prior to being inserted into the shortened balloon protective sleeve of FIG. 9.
Figure 12:
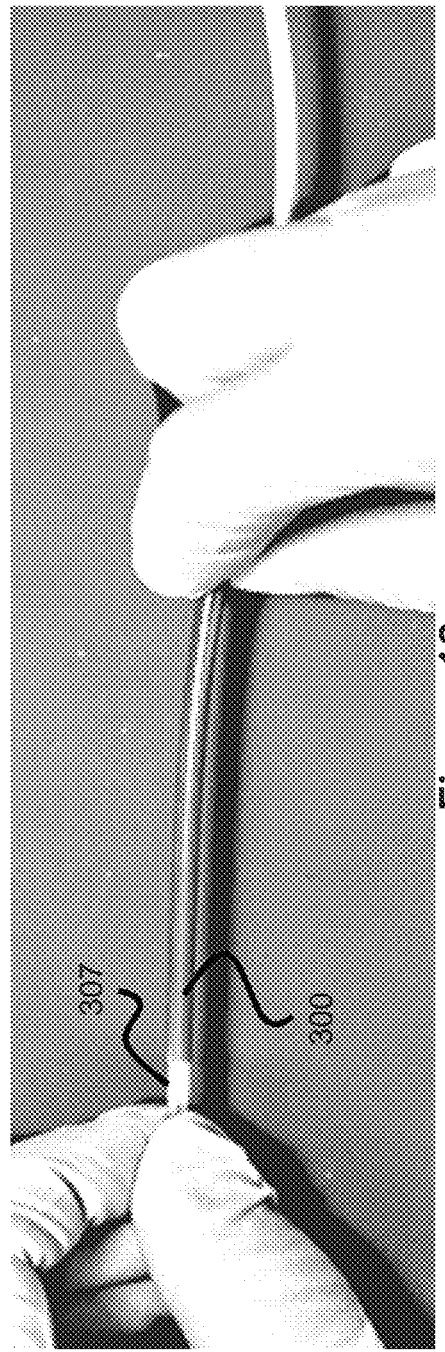
FIG. 12 illustrates a drug coated balloon being placed into the shortened balloon protective sleeve of FIG. 9.
Figure 13:
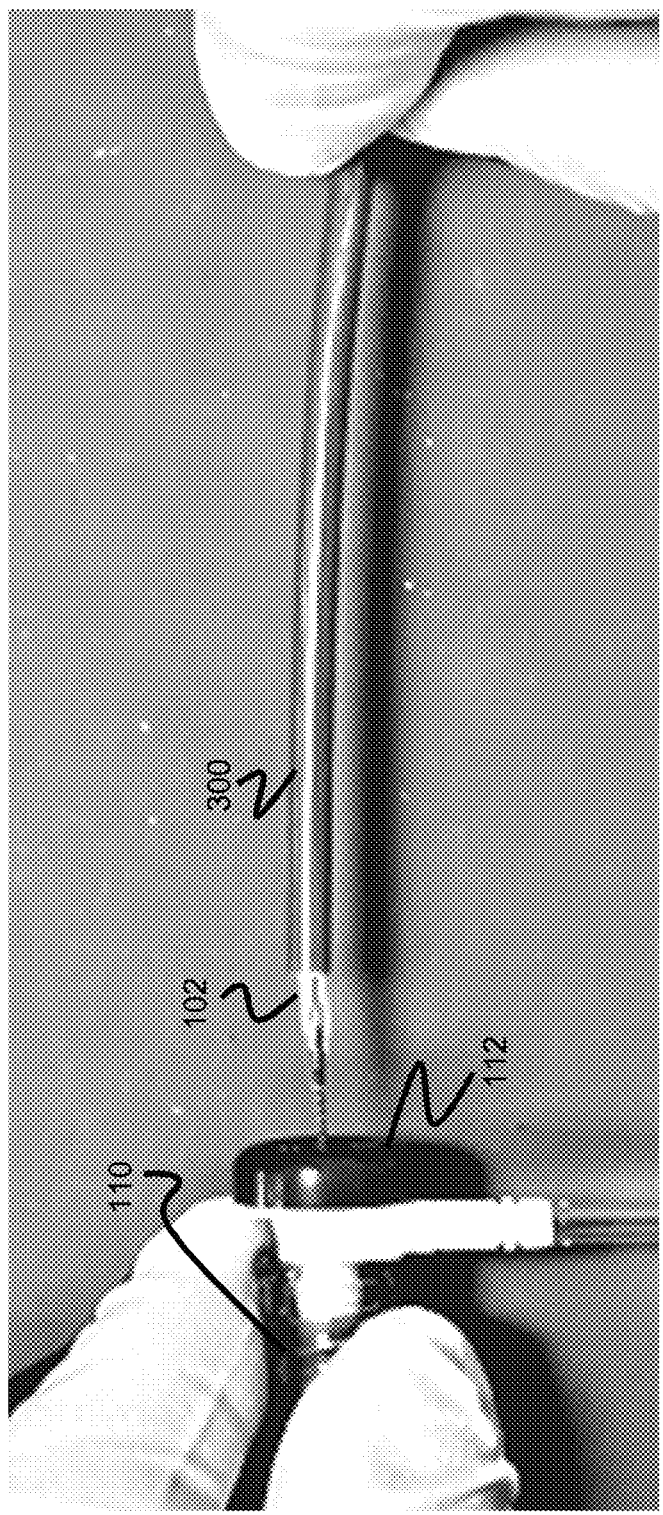
FIG. 13 illustrates a drug coated balloon with the shortened balloon protective sleeve of FIG. 9 being placed into the hemostasis valve of a guiding sheath.

The method of using protective sleeve 300 is shown in FIGS. 11-13. Please note, as pertains to the figures anything on the left side would be considered distal and anything on the right side would be considered proximal. Protective sleeve 300 is first removed from the proximal section of balloon catheter 103 so that the distal section of said balloon catheter 103 is later be placed through said protective sleeve 300. Due to the presence of the cut 301, this removal can occur by applying force against the cut 301 (referring to FIG. 10, one pulls upwards to remove sleeve 300 since cut 301 is located on the bottom of the sleeve 300).

Generally, drug coated balloons come pre-shipped in a protective tube 307 during shipping and handling to protect the drug after manufacture. This protective tube 307 must be removed prior to using the drug coated balloon/balloon catheter, prior to placement within the hemostasis valve of the guiding sheath. The distal part of the balloon catheter, which includes the drug coated balloon which is located at the distal end of the balloon catheter 103 around balloon catheter lumen 103 is shown in FIG. 11. The distal part of the balloon catheter including surrounding protective tube 307 is inserted through the protective sleeve 300, so that the distal part of the balloon catheter and distal part of protective tube 307 sits past the distal end of protective sleeve 300. Protective tube 307 is then pulled distally (to the left) as shown in FIG. 12 to remove the protective tube 300 from the balloon 102. After this, as shown in FIG. 13, the protective sleeve 300 is then placed within the hemostasis valve 112 of guiding sheath 110 so that the protective sleeve 300 is positioned through the entire hemostasis valve 112. The balloon catheter is then pushed distally (in a leftward direction) to propel the balloon 102 through the hemostasis valve 112 and into the guiding sheath 110. Once the entire balloon 102 is past the hemostasis valve 112 and is loaded into the guiding sheath, the protective sleeve 300 is proximally retracted (pulled to the right) and removed (e.g. by pulling against the cut, so pulling upwards in FIG. 13 to remove the entire sleeve 300) and the rest of the balloon catheter 103 is pushed through the hemostasis valve 112 and into the guiding sheath 110.

Alternative embodiments have a shortened protective sleeve 300 as a separate element that is unconnected to balloon catheter 103; however pre-placement on balloon catheter 103 would provide a more convenient format to locate the shortened protective sleeve 300 as part of a balloon catheter system or kit. Alternative embodiments may also utilize a pre-scored or pre-weakened region in place of cut 301, in which the user applies enough pressure to tear open region 301.

The primary benefit of insertion sleeve/protective sleeve 300 is that it protects the drug coated balloon 102 from contact with the reduced diameter and roughened area of the hemostasis valve 112, thus mitigating the issue of drug loss during placement through said hemostasis valve 112. One additional advantage of the cut section 301 of the protective sleeve 300 is that when the sleeve is placed into a small-diameter tube, the ends of the tube can overlap to fit the smaller profile. Since the hemostasis valve 112 has a reduced diameter compared to the rest of the guiding sheath, the protective sleeve 300 can curl over itself to fit this reduced diameter (meaning the protective sleeve 300 can conform to fit a much smaller diameter hemostasis valve—by contrast, a non-cut tube could not fit into a hemostasis valve with a smaller diameter than the tube for obvious reasons). The earlier description discussed one cause of drug loss being exposure to blood. The ability of the protective sleeve 300 to contract to fit the hemostasis valve 300 means there is less exposed surface area of the drug coated balloon available exposed to blood, further minimizing the chance of drug falling off the balloon during placement.

In the protective sleeve embodiments of FIGS. 1-8 in which the protective sleeve extends the length of the guiding sheath and includes a distal tubular section to support the drug coated balloon, the sleeves must be relatively long since they are positioned within the guiding sheath 110. The distal tubular sections 101, 201 must also be sized similar to the length of the drug coated balloons. Drug coated balloons 102 can be anywhere from 40-200 millimeters in length depending on the size of the vascular area treated, so the distal tubular sections 101, 201 must be at least this size to accommodate the balloon. One advantage of the insertion sleeve/protective sleeve 300 is that it is relatively short since it only must be large enough to span hemostasis valve 112 of the guiding sheath. In some examples, as discussed earlier, the protective sleeve 300 is about 3 inches, 7.62 centimeters, or about 8 centimeters in length.

Figure 14:
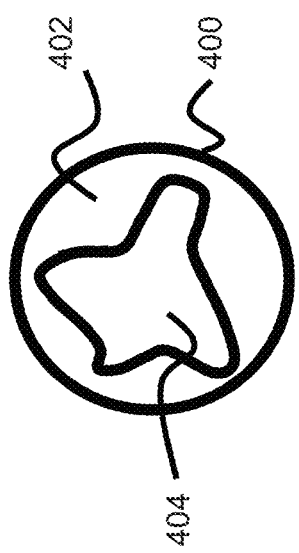
FIG. 14 illustrates a stenosis site within the vasculature.

When sclerotic material builds up in a vessel, it often adopts awkward shapes—as shown in the vessel cross section shown in FIG. 14 in which vessel 400 has sclerotic material 402 which leaves a smaller vessel cross section 404 for blood flow. The sclerotic buildup narrows the space that blood can flow through the vessel, diminishing blood flow through the vessel in a phenomenon called stenosis—which can cause a variety of complications. Typical treatment procedures can proceed in a couple ways. One treatment option uses a high-pressure balloon to inflate and compress the sclerosis to try to restore regular blood flow to the vessel. However, if the sclerosis is particularly dense or if stenosis keeps recurring (a phenomenon known as restenosis), this method is not useful.

A second treatment option is to use a drug-coated balloon to apply drug to the vessel wall and sclerotic material to try to treat the stenosis. However, the irregular profile of the sclerotic material can make it difficult to effectively apply the drug equally around the vessel since it would be difficult for the balloon to adopt the awkward shape to conform to vessel cross-section 404—in fact, inserting a drug coated balloon by itself would result in the drug-coated balloon only touching the "narrowest" part of the sclerotic region which is a very inefficient way to deliver the drugs. Additionally, the presence of a thick sclerotic layer would make it difficult for the drug to reach the wall of the blood vessel. Physicians often use a pre-dilation step to address this problem, where a first high-pressure balloon is inserted into the sclerotic region and expanded in order to compress the sclerosis and produce a consistent circular lumen—once there is a consistent circular lumen, it is much easier for the drug coated balloon to adopt a circular shape to treat the area. Once the pre-dilation step is completed a second balloon—a drug coated balloon which can be coated with anti-sclerotic drug such as Paclitaxel, Sirolimus, and/or Zotarolimus is then inserted and inflated to contact the sclerosis and vessel wall, and deliver drugs to said sclerosis and tissue. This procedure can take a substantial amount of time since a first balloon must be tracked through a guiding sheath and delivered to the target site and inflated for the pre-dilation step and then be deflated and withdrawn through the guiding sheath. Then a drug-coated balloon must be tracked through the guiding sheath and placed at the target site, expanded to deliver the drug, and then removed and withdrawn. The extra-step of pre-dilation takes extra time and can increase the risk of complications such as stroke in circumstances where there is significant narrowing of the blood vessels due to sclerosis. The following embodiments deal with a dual-balloon microcatheter system which includes both a dilation balloon and a compliant drug-coated balloon so that the dilation and drug delivery can take place simultaneously.

Figure 15:
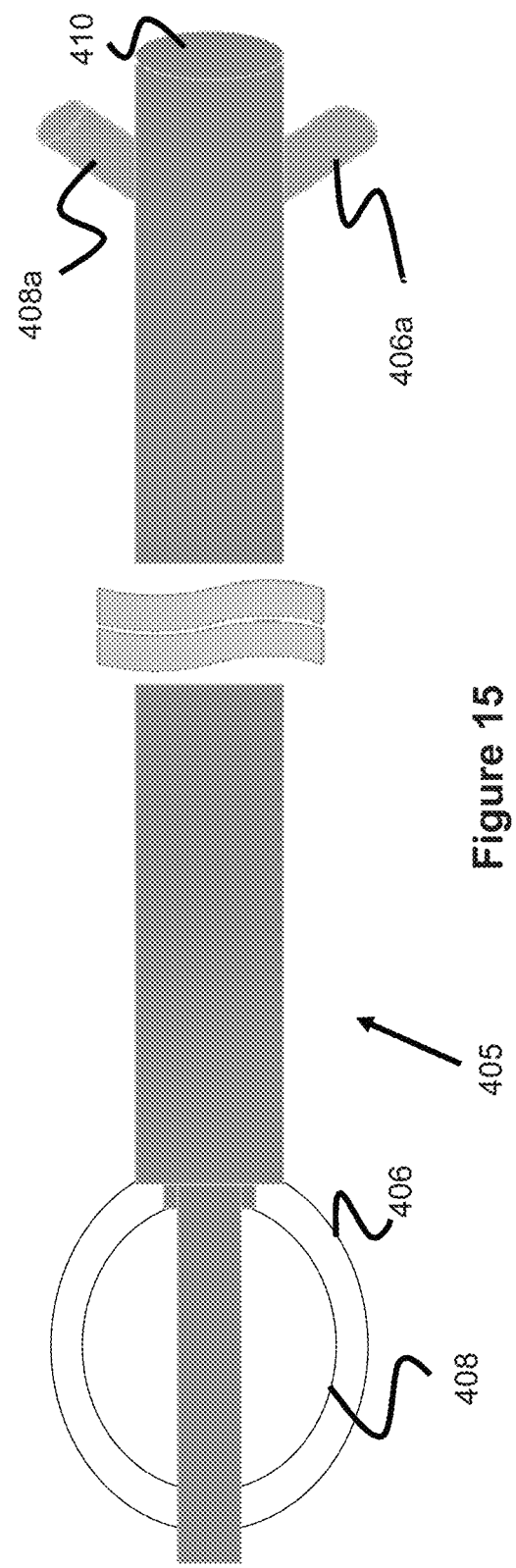
FIG. 15 illustrates a balloon catheter utilizing an inner and an outer balloon that can be used to treat the stenosis site of FIG. 14.

FIG. 15 illustrates a balloon catheter system 405 having two balloons. The two-balloon system utilizes an outer, primary, highly-compliant drug coated balloon 406 and an inner, secondary, high-pressure balloon 408. The inclusion of two balloons on one balloon catheter eliminates the need for a separate pre-dilation step since the inner balloon can dilate the vessel while the outer balloon can then conform to the stenosis after dilation and therefore there is no need for two separate balloon catheters and the time associated with tracking two separate balloon catheters through the vasculature to treat the stenosis.

In one embodiment, the two balloons are concentric, as is shown in FIG. 15. The balloon catheter contains two inflation lumens, one (408a) to inflate the inner balloon and the other (408b) to inflate the outer balloon—while a third lumen 410 provides access for a guidewire or additional therapeutic materials. Typical inflation media such as liquid contrast agent can be used to inflate the balloons. The inner balloon is a high-pressure balloon and should be high strength in order compress the sclerosis, thereby dilating the vessel. Conventional high-pressure balloon material such as nylon can be used for this inner/secondary balloon 408. The outer balloon 406 is highly conformable and is meant to conform to the shape of the sclerotic region in order to ensure even drug delivery throughout the entire sclerotic region. Soft, compliant material is therefore ideal for the inner/primary balloon; Polyblend 18-45 may be used for the inner/primary balloon.

The method of use of the dual-balloon catheter system 406 to treat a sclerotic region like the one shown in FIG. 14 is described, as follows. The primary, compliant outer drug-coated balloon 406 is first inflated and due to the compliant nature of the balloon, this balloon can generally conform to the shape of the sclerotic region to deliver drug to the region—however depending on the nature of the stenotic shape it may not completely comply with the shape if the shape is particularly complex or irregular. The physician can observe the treatment site through fluoroscopy to determine how well the compliant, drug-coated balloon conforms to the vessel shape. If dilation is needed to get a consistent, circular shape or to compress the sclerosis, then the primary, outer balloon 406 is deflated and the secondary, inner high-pressure balloon 408 is then inflated. Since the outer balloon 406 is located over the inner balloon 408, the outer balloon 406 maintains contact with the sclerosis, but the force from the inner-high pressure balloon further compresses the sclerosis and creates a consistent, open lumen for blood flow through the vessel. Note that even if outer drug-coated balloon 406 is complying to the stenosis shape, it may still be desirable to use a dilation procedure to decrease the amount of stenosis buildup and "open" up the vessel for blood flow—the inclusion of the high pressure inner balloon 408 allows this to be done while utilizing the same balloon catheter.

Other double balloon systems are additionally contemplated. For instance, a dual lumen inflation system can be used with two balloons where the balloons are positioned longitudinally adjacent with respect to each other (i.e., proximally/distally of each other). One balloon is a compliant drug-coated balloon, and a second linearly displaced balloon is a high-pressure balloon. With this system, the balloons can be used in either order (e.g. either the compliant, drug-coated balloon or the high-pressure balloon could be inflated and used first). The catheter can be linearly moved so that either the first balloon or the second balloon is aligned with the sclerotic region.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon catheter adapted for inserting a drug-coated balloon through a hemostasis valve of a guiding sheath comprising: a catheter body having the drug-coated balloon disposed at a distal end of the catheter body; a strain relief near a proximal end of the balloon catheter; a slit sleeve removably mounted to the strain relief; a longitudinal opening extending along an entire length of only a side of the slit sleeve; the slit sleeve forming a generally tubular shape and having a first non-flared section in which the longitudinal opening has a first width and a second flared end section in which the longitudinal opening has a second width that is larger than the first width and that increases in width in a direction away from the first non-flared section, where the second flared end section is sized to be positioned over a portion of the strain relief; wherein the slit sleeve is configured to be removed from the strain relief and is configured to be inserted through the hemostasis valve of the guiding sheath to protect the drug-coated balloon as the drug-coated balloon is inserted through the hemostasis valve; and wherein the first width of the longitudinal opening in the first non-flared section of the slit sleeve is about 0.002 inch.

2. The balloon catheter of claim 1, wherein the drug-coated balloon is coated with one of Paclitaxel, Sirolimus, or Zotarolimus.

3. The balloon catheter of claim 1, wherein the second width of the longitudinal opening in the second flared end section of the slit sleeve is tapered and has a maximum opening size of 0.17 inches to 0.23 inches.

4. The balloon catheter of claim 1, wherein the second flared end section of the slit sleeve has a diameter of 0.285 inches to 0.345 inches.

5. The balloon catheter of claim 1, wherein the first non-flared section of the slit sleeve has a diameter of 0.115 inches to 0.12 inches.

6. The balloon catheter of claim 1, wherein the second flared end section of the slit sleeve has a length of 0.5 inches to 1 inch.

7. The balloon catheter of claim 1, wherein the slit sleeve has a length of 2.75 inches to 3.75 inches.

8. The balloon catheter of claim 1, wherein the slit sleeve is composed of a polymeric material.

9. The balloon catheter of claim 1, wherein the second flared end section of the slit sleeve is configured to sit over the strain relief of the balloon catheter.

10. The balloon catheter of claim 1, further comprising a protective tube over the drug coated balloon.

11. The balloon catheter of claim 10, wherein the slit sleeve is sized to fit over the protective tube, to aid in removing the protective tube prior to inserting the drug coated balloon through the hemostasis valve of the guiding sheath.

12. The balloon catheter of claim 10, wherein the slit sleeve has a larger diameter than that of the protective tube.

13. A balloon catheter adapted for removing a protective tube from a drug coated balloon prior to inserting the drug-coated balloon through a hemostasis valve of a guiding sheath comprising: a catheter body having the drug-coated balloon disposed at a distal end of the catheter body; and wherein the protective tube is positioned over the drug-coated balloon; a strain relief near a proximal end of the balloon catheter; a slit sleeve removably mounted to the strain relief; a longitudinal opening extending along an entire length of only a side of the slit sleeve; the slit sleeve forming a generally tubular shape and having a first non-flared section in which the longitudinal opening has a first width, and a second flared end section in which the longitudinal opening has a second width that is larger than the first width such that it increases in size in a direction away from the first non-flared section, where the second flared end section is sized to be positioned over a portion of the strain relief; wherein the slit sleeve is configured to be removed from the strain relief and is configured to be inserted through the hemostasis valve of the guiding sheath to protect the drug-coated balloon as the drug-coated balloon is inserted through the hemostasis valve; and wherein the first width of the longitudinal opening in the first non-flared section of the slit sleeve is about 0.002 inch.

14. The balloon catheter of claim 13, wherein the slit sleeve is further configured to be inserted through the hemostasis valve of the guiding sheath to protect the drug-coated balloon as the drug-coated balloon is inserted through the hemostasis valve.

15. A drug-coated balloon adapted for insertion through a hemostasis valve of a guiding sheath comprising: the drug coated balloon on a distal portion of a balloon catheter, a protective tube over the drug coated balloon; a sleeve mounted to a strain relief near a proximal end of the balloon catheter and adapted to be removed from the strain relief; the sleeve having a slit extending entirely along a length of the sleeve and only along a side of the sleeve; the slit having a first portion with a uniform width and a second portion being tapered in increasing width in a direction away from the first portion; wherein the sleeve is configured first to be placed over the protective tube to allow the protective tube to be removed from the drug coated balloon, and then to be placed into the hemostasis valve of the guiding sheath to protect the drug-coated balloon as the drug coated balloon is inserted through the hemostasis valve; wherein the first portion of the slit width is about 0.002 inch.

16. The drug-coated balloon of claim 15, wherein the slit of the second portion forms a "V" shape.

* * * * *